United States Patent [19]

Wataya et al.

[11] 4,005,151

[45] Jan. 25, 1977

[54] PROCESS FOR PRODUCING POLYHALOGENATED PHENOLS

[75] Inventors: Masataka Wataya, Nagareyama; Nobuo Onodera, Hiratsuka; Shosuke Imamura, Yokohama, all of Japan

[73] Assignee: Hodogaya Chemical Co., Ltd., Tokyo, Japan

[22] Filed: Mar. 5, 1975

[21] Appl. No.: 555,627

[30] Foreign Application Priority Data

Mar. 7, 1974 Japan .............................. 49-25755

[52] U.S. Cl. .......................................... 260/623 R
[51] Int. Cl.² ................... C07C 39/30; C07C 39/32
[58] Field of Search .................. 260/623 R, 621 M

[56] References Cited

UNITED STATES PATENTS

| | | | |
|---|---|---|---|
| 1,910,679 | 5/1933 | Crawford et al. ............. | 260/621 M |
| 2,489,423 | 9/1949 | Lawson et al. ................ | 260/623 R |

*Primary Examiner*—James O. Thomas, Jr.
*Assistant Examiner*—W. B. Lone
*Attorney, Agent, or Firm*—Cushman, Darby & Cushman

[57] ABSTRACT

A process for producing polyhalogenated phenol by mixing a polyhalogenated aniline with an aqueous sulfuric acid solution to obtain a suspension of fine particles of polyhalogenated aniline sulfate having the particle size of 50 $\mu$ or less, diazotizing the polyhalogenated aniline sulfate to obtain polyhalogenate benzenediazonium sulfate, hydrolyzing the resulting benzenediazonium sulfate by heating it as such, recycling to the diazotization step the aqueous sulfuric acid solution from which the desired polyhalogenated phenol has been separated.

10 Claims, No Drawings

PROCESS FOR PRODUCING POLYHALOGENATED PHENOLS

The present invention relates to a process for producing polyhalogenated phenols which are useful as intermediates for agricultural chemicals and as the raw materials for other industrial chemicals.

As to the production of polyhalogenated phenols, there are various processes have been proposed. For example, direct halogenation of phenol has been known. However, according to this direct halogenation, two or three halogen atoms cannot be introduced to the desired positions in the molecule of the phenol due to the orientation effects of the hydroxy group. Alternatively, so-called "indirect method" for producing polyhalogenated phenols has been proposed. According to this indirect method, the hydroxy group may be introduced into benzene structure to form the phenol at the final step in the method.

In addition, a process for obtaining polyhalogenated phenols by diazotizing the corresponding polyhalogenated aniline in a mineral acid, and hydrolyzing the diazotized aniline under heating (hereinafter referred to as diazo-decomposition method) is also known as an indirect method. According to this diazo-decomposition method, phenols having substituted groups at the desired positions can be produced.

In commercial production, however, when a polyhalogenated phenol is produced by the diazo-decomposition method, there are many drawbacks. Furthermore, from the controlling of an environmental disruption standpoint, since a large amount of waste acid is produced as a by-product, the diazo-decomposition method is not considered to be a suitable method for commercial production.

In prior art references, (for example, Ber. 38, 3510, Rec. trav. chim., 50, 112–120), there is disclosed a process for producing a polyhalogenated phenol by diazotizing polyhalogenated aniline in a concentrated sulfuric acid, then the diazotized product is hydrolyzed in an aqueous sulfuric acid. The feature of this process is that the diazotization of polyhalogenated aniline having a weak basicity is carried out in a concentrated sulfuric acid for the purpose of to attain higher diazotization yield. In this process, however, the hydrolysis of the diazotized product is carried out in a diluted sulfuric acid solution and the diluted sulfuric acid thus produced as a by-product cannot be reused as it is for the diazotization purpose. In other words, a large amount of diluted sulfuric acid comes out as a waste acid after the process. The diluted sulfuric acid thus formed as a by-product is discarded as a waste acid or is to be recovered as a concentrated sulfuric acid by using an expensive equipment for the concentration.

As explained above, the diazo-decomposition method does not seem an excellent method for producing polyhalogenated phenol from industrial standpoint. However, from the reaction theory standpoint, this diazo-decomposition method is considered to be an excellent method. The present inventors have made extensive studies on diazo-decomposition method for the purpose of providing it to an industrial scale production, they found the fact that polyhalogenated phenols can be produced from the corresponding polyhalogenated aniline through diazotization process, without the formation of waste sulfuric acid as a byproduct.

The object of the present invention is to provide a process for producing polyhalogenated phenol represented by the formula,

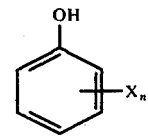

wherein X is chlorine or bromine atom and $n$ is 2 or 3, by mixing a polyhalogenated aniline represented by the formula,

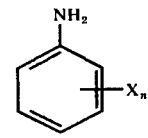

wherein X and $n$ are the same as defined above, with an aqueous sulfuric acid solution, to obtain the polyhalogenated aniline sulfate, pulverizing the polyhalogenated aniline sulfate according to a wet pulverizing process to obtain a suspension of fine particles of polyhalogenated aniline sulfate having a particle size of 50 $\mu$ or less, adding sodium nitrite to the polyhalogenated aniline sulfate suspension to effect the diazotization of the polyhalogenated aniline sulfate, then hydrolyzing the resulting benzenediazonium sulfate by heating it as such and recycling to the diazotization step the aqueous sulfuric acid solution from which the desired polyhalogenated phenol has been separated.

According to a process of the present invention, the diazotization (the first reaction) of polyhalogenated aniline is carried out in an aqueous sulfuric acid medium and then the hydrolysis (the second reaction) is carried out by heating the diazotization mixture as such to produce the desired polyhalogenated phenol. The desired polyhalogenated phenol is then separated from the hydrolysis mixture. On the other hand, the aqueous sulfuric acid solution recovered and isolated from the hydrolysis mixture can be re-used to the first reaction, since the water content of the sulfuric acid solution was not changed necessarily during the two reactions. Thus, the feature of the present process is that there is no formation of diluted sulfuric acid to be wasted.

More particularly, when a polyhalogenated aniline sulfate is diazotized in an aqueous sulfuric acid solution, the solubility of the polyhalogenated aniline sulfate in the aqueous sulfuric acid solution is very low, thus a large amount of the aqueous sulfuric acid is required for carrying out the diazotization in homogeneous system. However, such process is not suitable for a commercial production. In the process of the present invention, it is not advisable to carry out the diazotization in a diluted sulfuric acid for the purpose of keeping the hydrolysis at a suitable temperature, since both the diazotization and hydrolysis are carried out in aqueous sulfuric acid solution of the same concentration. When diazotization of polyhalogenated aniline sulfate is carried out in an aqueous sulfuric acid solution in an amount at least industrially allowable, the diazotization can only be carried out in a heterogeneous suspension state. In such a case, even if the diazotization is carried out with a good stirring condition by adding polyhalogenated aniline into an aqueous acid at a specific temperature and then adding sodium nitrite into the reaction mixture at a suitable temperature, the diazotization of polyhalogenated aniline can only proceed at a lower level. Alternatively, for the purpose of carrying out the diazotization at a higher level, it should be carried out in a concentrated sulfuric acid medium. According to the extensive studies on the diazotization in an aqueous sulfuric acid medium made by the present inventors, it is found that the diazotized product can be obtained in quantitative yield by adding polyhalogenated aniline into an aqueous sulfuric acid, pulverizing the polyhalogenated aniline sulfate according to a wet pulverizing process to obtain a suspension of fine particles of polyhalogenated aniline sulfate and diazotizing the sulfate at a suitable temperature.

In this connection, the particular size of the polyhalogenated aniline sulfate is closely related to the diazotization yield, thus larger particle size of the polyhalogenated aniline sulfate decreases the diazotization yield. In the process of the present invention, the particle size of the polyhalogenated aniline sulfate is to be 50 $\mu$ or less. When at least 95% of the particles have the particle size of 20 $\mu$ or less, the diazotization can be proceed quantitatively.

A suspension of fine particles of the polyhalogenated aniline sulfate can be prepared within few hours by treating any type of pulverizing equipment, such as a ball mill, in wet process. The pulverizing methods are not limited to such equipment, the only importance is to obtain a suspension of fine particles having particle size in the preferable range.

The concentration of the aqueous sulfuric acid solution can be selected widely with regard to diazotization. However, it is advisable to select the concentration to a suitable range for hydrolysis. Thus, an aqueous sulfuric acid solution having the concentration of 10–80% can be used. Particularly a concentration of 40–75% is preferable.

Sulfuric acid used in the present process activates the sodium nitrite to produce nitrous acid and forms the acid moiety of the diazonium salt formed. Furthermore, the sulfuric acid also acts as the solvent, the amounts of sulfuric acid to be used is closely related to the concentration thereof. Preferably, 3–50 moles of sulfuric acid on the basis of the amounts of polyhalogenated aniline is to be used.

The amount of sodium nitrite to be used is the equivalent or slightly excess amounts of the polyhalogenated aniline. In this connection, either a powder form or a concentrated aqueous solution of sodium nitrite can be used. For the purpose of keeping constant the concentration of the aqueous sulfuric acid solution, the powder form of sodium nitrite is preferable. In case an aqueous solution of sodium nitrite is to be used, as higher as possible concentrated solution should be used.

The diazotization in the present invention is carried out at a temperature of −10° to 40° C. It is preferable to carry out at a temperature of 10° to 30° C. The diazotization usually proceeds at a fast rate and is generally completed within a few hours.

Next, the thus prepared diazonium salt is hydrolyzed by heating to obtain the corresponding polyhalogenated phenol, if necessary, urea or sulfamic acid can be added for the purpose of to decompose nitrous acid remaining in the diazotized mixture.

Hydrolysis of the diazonium salt can be carried out advantageously in the presence of an organic solvent, such as toluene, xylene or o-chlorotoluene which can forms a heterogeneous layer with the aqueous sulfuric acid solution, to obtain the desired polyhalogenated phenol in higher yeild, for example over 80%. A method for heating the diazotized solution is that heating the solution gradually to keep it at suitable temperature, or adding the diazotized solution dropwise into a reaction vessel in which the solvent is kept at a suitable temperature. The reaction temperature can be selected from 90° C to an apparent boiling temperature of the aqueous sulfuric acid solution used. Preferably the reaction can be carried out at 110° – 160° C and more preferably at 120° – 150° C.

The hydrolysis time required to complete the reaction is varied depend upon the amount of the reactant, method of reaction or reaction temperature and usually it is required for about 4 to 5 hours.

The desired polyhalogenated phenol formed in the hydrolysis is isolated by separating the aqueous sulfuric acid layer from the hydrolysis product in case the hydrolysis was carried out in the presence of an organic solvent. Alternatively, in case the hydrolysis was carried out in the absence of an organic solvent, the desired polyhalogenated phenol formed in the hydrolysis product is extracted with an organic solvent and isolated by removing the organic solvent by distillation.

Some of the polyhalogenated phenol can easily be isolated by a method of steam distillation. In this instance, the hydrolyzed product is kept at a temperature suitable for maintaining the concentration of the sulfuric acid constant and superheated steam introduced into the hydrolyzed product to distill off the desired polyhalogenated phenol. Among the methods for isolation of the desired polyhalogenated phenol, the solvent extraction method is most preferable.

The aqueous sulfuric acid solution separated from the hydrolysis product in the present process is kept at the same concentration throughout the first and the second reactions, since the sulfuric acid is not physically diluted such as addition of water. In other words, the concentration of the sulfuric acid can be kept at the same level by adding an adequate amount of sulfuric acid which is corresponding to the amount of sulfuric acid consumed in the first reaction.

On the other hand, a concentration of the inorganic salts formed by the reaction of sodium nitrite with sulfuric acid in the diazotization becomes higher. The inorganic salts thus formed may not give any adverse effect to the reactions but preferably are removed by filtration after cooling.

Among polyhalogenated phenols, the following compounds are advantageously produced by the process according the present invention.

2,3-Dichlorophenol
3,4-Dichlorophenol
2,5-Dichlorophenol
3,5-Dichlorophenol
2,4,5-Trichlorophenol
3,4,5-Trichlorophenol
3,4-Dibromophenol
2,5-Dibromophenol
3,5-Dibromophenol
2,4,5-Tribromophenol The following examples are given to illustrate specific embodiments of the present invention, and are not to be construed to limit the scope of the invention defined in the claims.

EXAMPLE 1

40 Grams of 3,4-dichloroaniline and 250 g of 60% aqueous sulfuric acid solution were charged together with ceramic balls into a ceramic ball mill having one liter capacity and the mill was rotated at 70 r.p.m. for 2 hours. The particle size of the thus obtained fine particles of 3,4-dichloroaniline sulfate were measured by means of an optical microscope. The average particle size was 2.1 $\mu$ and the standard deviation was 0.6 $\mu$.

EXAMPLE 2

A suspension of fine particles of 3,4-dichloroaniline sulfate was prepared by a method similar to that described in Example 1 and the ball mill used was washed with 156 g of 60% aqueous sulfuric acid solution. The suspension and the aqueous sulfuric acid washings were transferred into a diazotization vessel. The mixture in the vessel was cooled with stirring and was kept at 10° – 20° C, and 19.8 g of sodium nitrite powder was added in 30 minutes. The reaction mixture was stirred for 30 minutes at the same temperature. Then an adequate amount of sulfamic acid was added to decompose a small amount of nitrous acid remaining in the reaction system. Next, water was added to the reaction mixture under cooling to make the whole amount of the mixture to one liter. A very small amount of impurities contained in the mixture was removed by filtration. 100 Milliliters of the filtrate was diluted with water to make the whole volume to 250 ml. Thus, a diazo solution sample for analysis was obtained.

On the other hand, 15 ml of 0.1 M-$\beta$-naphthol solution and 20 ml of 1N-sodium carbonate solution were charged into a 100 ml beaker. The mixture of the solutions were stirred by means of a magnetic stirrer and the diazo solution sample was added dropwise from a burette to couple the $\beta$-naphthol. The equivalence point was determined by dropping a drop of the contents of the beaker onto the spot of H-acid in an N-sodium carbonate solution on a filter paper. The equivalence point was found when red coloration continued for two minutes. Thus, diazotization yield was found to be 97.2%.

EXAMPLE 3

410 Grams of 60% aqueous sulfuric acid solution was charged into a beaker having one liter capacity. Under stirring efficiently, 40 g of 3,4-dichloroaniline which was crushed and was passed 10 mesh sieve was added into the beaker to prepare a suspension of 3,4-dichloroaniline sulfate, and 19.8 g of sodium nitrite power was added in 30 minutes at 10°– 20° C. The reaction mixture was kept at the same temperature for one hour with stirring, then an adequate amount of sulfamic acid was added to decompose the remaining nitrous acid in the reaction mixture.

Next, water was added under cooling to make the whole volume of the mixture to one liter. Impurities contained in the mixture was removed by filtration. 100 Milliliters of the filtrate was diluted with water to make the whole volume of the diluted solution to 250 ml. The diluted solution was stored as a diazotized solution for analytical purpose. The diazotization yield was found to be 37.2% which was determined by a method similar to that described in Example 2.

EXAMPLE 4

400 Grams of 60% aqueous sulfuric acid solution and 40 g of 3,4-dichloroaniline which was previously crushed in mortar and passed through 10 mesh sieve, were charged together with ceramic balls into a ceramic ball mill having one liter capacity. A suspension of fine particles of 3,4-dichloroaniline sulfate was prepared by rotating the ball mill at 70 r.p.m. for 10 minutes. The fine particles of 3,4-dichloroaniline sulfate were fractionated by a gravitational precipitation method. The total amount of the fine particles having the particle size of 50 $\mu$ or less was 64.2% of the theoretical amount of 3,4-dichloroaniline sulfate to be formed.

On the other hand, a suspension of fine particles of 3,4-dichloroaniline sulfate was prepared by the same way as mentioned above, and was cooled with stirring and was kept at 10° –20° C. 19.8 Grams of sodium nitrite powder was added in 25 minutes. The reaction mixture was stirred at the same temperature for one hour and adequate amount of sulfamic acid was added to decompose nitrous acid remaining in the reaction mixture. The reaction mixture was then diluted with water under cooling to make the total volume of the diluted solution to one liter. Impurities contained in the diluted solution were removed by filtration. 100 Milliliters of the filtrate was diluted with water to make the whole volume of the diluted solution to 250 ml. The diluted solution was stored as a diazotized solution for analytical purpose. Diazotization yield was found to be 57.7% which was determined by a method similar to that described in Example 2.

EXAMPLE 5

40 Grams of 3,4-dichloroaniline and 250 g of 60% aqueous sulfuric acid solution were charged together with ceramic balls into a ball mill having one liter capacity. The ball mill was rotated at 70 r.p.m. for 2 hours to obtain a suspension of fine particles of 3,4-dichloroaniline sulfate. The suspension was transferred into a beaker having one liter capacity. The ceramic ball mill used was washed with 156 g of 60% aqueous sulfuric acid solution and the washings were also poured into the beaker. A mixture of the suspension and the washings were cooled with stirring and kept at 10° –20° C, and 19.8 g of sodium nitrite powder was added in 30 minutes. After the reaction mixture was stirred at the same temperature for 30 minutes, an adequate amount sulfamic acid was added to decompose nitrous acid remaining in the reaction mixture.

Next, 200 ml of xylene was charged into a flask having one liter capacity provided with a reflux condenser and was refluxed. The diazotized reaction mixture was added dropwise into the flask over 1.5 hours. The temperature was kept at 120° –130° C during the addition. After the addition of the mixture, the stirring was continued for 30 minutes at the same temperature to complete the reaction. The reaction mixture was cooled and the xylene layer was taken out. After the xylene was removed by distillation, 32.6 grams of 3,4-dichlorophenol (115°–122° C/10 mmHg) was obtained. The yield was found to be 81%. The amount of sulfuric acid recovered was 94.7% of theory.

EXAMPLE 6

40 Grams of 2,4,5-trichloroaniline and 200 g of 75% aqueous sulfuric acid solution were charged together with ceramic balls into a ceramic ball mill having one liter capacity. A suspension of fine particles of 2,4,5-trichloroaniline sulfate was prepared by a method similar to that described in Example 5. The suspension was transferred into a beaker having one liter capacity. The ceramic ball mill used was washed with 76 g of 75% aqueous sulfuric acid solution and the washings were also poured into the beaker. Diazotization of 2,4,5-trichloroaniline sulfate in the form of suspension of fine particles was carried out by a method similar to that described in Example 5 except that 15.5 g of sodium nitrite powder was added in 25 minutes. The diazotized solution was then hydrolyzed by a method similar to that described in Example 5. 33.0 g Grams of 2,4,5-trichlorophenol (115° – 120° C/10 mmHg) was obtained. The yield was found to be 82.0%.

EXAMPLE 7

40 Grams of 2,5-dichloroaniline and 250 g of 75% aqueous sulfuric acid solution were charged into a ceramic ball mill having one liter capacity. A suspension of fine particles of 2,5-dichloroaniline sulfate was prepared by a method similar to that described in Example 5. The suspension was transferred into a beaker having one liter capacity. The ceramic ball mill used was washed with 77 g of 75% aqueous sulfuric acid solution and the washings were transferred into the beaker. Diazotization of 2,5-dichloroaniline sulfate in the form of suspension of fine particles was carried out by a method similar to that described in Example 5 except that 18.2 g of sodium nitrite powder was added in 15 minutes. The diazotized solution was hydrolyzed by a method similar to that described in Example 5. 35.5 Grams of 2,5-dichlorophenol (100° – 105° C/20 mmHg) was obtained. The yield was found to be 88.3%.

EXAMPLE 8

61.6 Grams of 2,5-dibromoaniline and 250 g of 75% aqueous sulfuric acid solution were charged into a ceramic ball mill having one liter capacity. A suspension of fine particles of 2,5-dibromoaniline sulfate was prepared by a method similar to that described in Example 5. The suspension was transferred into a beaker having one liter capacity. The ceramic ball mill used was washed with 120 g of 75% aqueous sulfuric acid solution and the washings were transferred into the beaker. Diazotization of 2,5-dibromoaniline sulfate in the form of suspension of fine particles was carried out by a method similar to that described in Example 5 except that 18.2 g of sodium nitrite powder was added. Hydrolysis of 2,5-dibromobenzenediazonium sulfate was carried out by a method similar to that described in Example 5. A xylene layer was isolated from the hydrolyzed product and a crude product of 2,5-dibromophenol was obtained after the xylene was removed by distillation. The crude product of 2,5-dibromophenol was steam distilled by introducing superheated steam. After the distillate was cooled, crystallized 2,5-dibromophenol thus formed was obtained by filtration and dried. 47.3 Grams of 2,5-dibromophenol having melting point of 71°–74° C was obtained. The yield was found to be 85.0%.

EXAMPLE 9

3,4-Dichloroaniline was treated with 60% of aqueous sulfuric acid solution which was recovered from Example 5 by a method similar to that described in Example 5. After diazotization, inorganic crystals formed in the diazotization was removed by filtration and the filtrate thus obtained as hydrolyzed and treated by a method similar to those described in Example 5. 32.4 Grams of 3,4-dichlorophenol (118° – 122° C/10 mmHg) was obtained. The yield was found to be 80.5%.

EXAMPLE 10

40 Grams of 3,4-dichloroaniline and 150 g of 75% aqueous sulfuric acid solution were charged together with ceramic balls into a ceramic ball mill having one liter capacity. The pulverization was carried out as in Example 1 to obtain a suspension of fine particles of 3,4-dichloroaniline sulfate. The suspension was transferred into a beaker having one liter capacity. The ceramic ball mill was washed with 100 g of 75% aqueous sulfuric acid solution and the washings were also poured into the beaker. Diazotization was carried out by adding 19.8 g of sodium nitrite as in Example 1. The diazo solution thus obtained was charged into a flask having one liter capacity and heated gradually to 75° –120° C in 20 minutes with good stirring, then additionally heated to 120° – 130° C in 20 minutes and further heated to 130° – 135° C for 4 hours to complete the hydrolysis. The reaction mixture was then cooled and 200 ml of xylene was added thereto with stirring. The xylene layer was isolated from the reaction mixture and a crude product of 3,4-dichlorophenol was obtained after the xylene was removed by distillation. The crude product was then distilled under a reduced pressure to obtain 27.9 g of 3,4-dichlorophenol (115° – 122° C/10 mmHg). The yield was found to be 69.3%.

What is claimed is:

1. In a process for producing a polyhalogenated phenol represented by the formula,

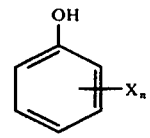

wherein X is chlorine or bromine atom and n is 2 to 3, diazotizing a polyhalogenated aniline represented by the formula,

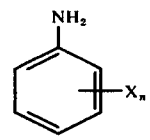

wherein X and n are as defined above to obtain a benzenediazonium salt and hydrolyzing the benzenediazonium salt to obtain the polyhalogenated phenol, the improvement which comprises mixing the polyhalogenated aniline with an aqueous sulfuric acid solution to obtain the polyhalogenated aniline sulfate, pulverizing the polyhalogenated aniline sulfate according to a wet pulverizing process to obtain a suspension of fine particles of the polyhalogenated aniline sulfate having a particle size of 2 to 50 microns, adding sodium nitrite to the polyhalogenated aniline sulfate suspension and effecting the diazotization of the polyhalogenated aniline sulfate at −10° C to +40° C, hydrolyzing the resulting polyhalogenated benzenediazonium sulfate by heating it as such at a temperature from 90° C to the apparent boiling temperature of the aqueous sulfuric acid and recycling to the diazotization step the aqueous sulfuric acid solution from which the desired polyhalogenated phenol has been separated.

2. A process according to claim 1, wherein the aqueous sulfuric acid solution has a concentration of 10 to 80 per cent.

3. A process according to claim 2, wherein the concentration of the aqueous sulfuric acid solution is 40 – 75 per cent.

4. A process according to claim 1, wherein the aqueous sulfuric acid solution is used in an amount of 3 to 50 moles on the basis of the amount of polyhalogenated aniline to be used.

5. A process according to claim 1, wherein the hydrolysis of the polyhalogenated benzenediazonium sulfate is carried out in the presence of an organic solvent.

6. A process according to claim 1 wherein the diazotization is carried out at +10° to +30° C. and the hydrolysis is carried out at 110° to 160° C.

7. A process according to claim 6 wherein the hydrolysis is carried out at 120° to 150° C.

8. A process according to claim 1 wherein the hydrolysis is carried out in the presence of an organic solvent selected from the group consisting of toluene, xylene and o-chlorotoluene.

9. A process according to claim 1 wherein at least 95% of the particles have a particle size of not over 20 microns.

10. A process according to claim 9 wherein the particle size is 2 microns.

* * * * *